United States Patent [19]

Namiki et al.

[11] Patent Number: 4,774,343

[45] Date of Patent: Sep. 27, 1988

[54] METHOD OF PRODUCING ACTIVE ANTIOXIDANT

[75] Inventors: Mitsuo Namiki; Toshihiko Osawa; Minoru Isobe; Yasuko Fukuda, all of Aichi, Japan

[73] Assignee: Takemoto Yushi Kabushiki Kaisha, Aichi, Japan

[21] Appl. No.: 32,182

[22] Filed: Mar. 30, 1987

[30] Foreign Application Priority Data

Mar. 31, 1986 [JP] Japan .................................. 61-75361

[51] Int. Cl.⁴ ........................................... C07D 493/04
[52] U.S. Cl. .................................................... 549/435
[58] Field of Search ........................................ 549/435

[56] References Cited

U.S. PATENT DOCUMENTS 2,837,534  6/1958  Tracy ................................. 549/435
4,649,206  3/1987  Namiki et al. ..................... 549/435

*Primary Examiner*—J. R. Brown
*Assistant Examiner*—Wendy B. Davis
*Attorney, Agent, or Firm*—Flehr, Hohbach, Test, Albritton & Herbert

[57] ABSTRACT

An active antioxydant containing a compound shown by structural formula

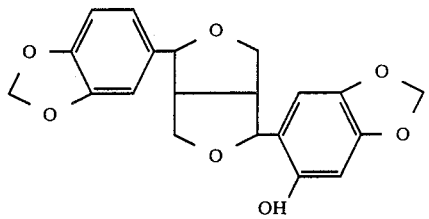

is produced by applying an acid catalyst to sesamolin substantially in the absence of active hydrogen compounds.

13 Claims, No Drawings

METHOD OF PRODUCING ACTIVE ANTIOXIDANT

BACKGROUND OF THE INVENTION

This invention relates to a method of producing an active antioxydant containing a compound which is derived from sesamolin and has the following structural formula (A) (hereinafter referred to as Compound A):

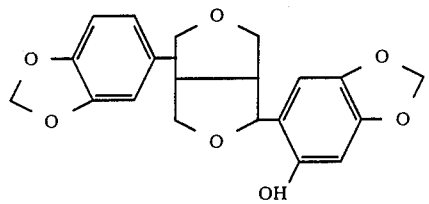

As an active antioxydant derived from sesamolin, sesamol which is obtained by hydrolysis of sesamolin has long been known. Antioxydative activity of sesamol, however, is rather weak. Since sesamol has a small molecular weight, it evaporates at a temperature of about 100° C., and its antioxydative activity is practically nonexistent in the range of cooking temperature from 160° to 180° C. at which, for example, frying is done. Compound A is a naturally-occurring active antioxydant and its presence in Justicia Simplex which is used as a medicinal herb in the Himalayan regions and sesame seeds has recently been reported (for example, in *Phytochemistry*, 19, 322 (1980)). Methods of obtaining Compound A by extracting and separating it from Justicia Simplex and sesame seeds have been considered but since the content of Compound A is only about 20 ppm in Justicia Simplex and about 15 ppm in sesame seeds, it is economically not feasible to rely on such a simple extraction-separation process on an industrial scale. The present inventors have already disclosed that Compound A can be obtained by hydrolysis of a glycoside extracted from sesame seeds with β-glucosidase (Japanese Patent Application Tokkai No. 59-157173). This method, too, is difficult to apply industrially, however, because the content of Compound A in glycoside is small and complicated operations for partial extraction are required.

SUMMARY OF THE INVENTION

It is therefore an object of the present invention to eliminate the aforementioned problems and to provide a method of producing a new active antioxydant.

It is another object of the present invention to provide an industrially feasible method of producing aforementioned Compound A.

The above objects are achieved by the present invention which was completed on the basis of the discovery by the present inventors that Compound A is obtained by rearrangement of sesamolin if an acid catalyst is applied to sesamolin with substantially no participation by active hydrogen compound in the reaction.

DETAILED DESCRIPTION OF THE INVENTION

The present invention discloses a method of producing an active antioxydant characterized in that Compound a is obtained by rearrangement of sesamolin as shown below by application of an acid catalyst to sesamolin under the condition of substantially no participation by active hydrogen compounds in the reaction:

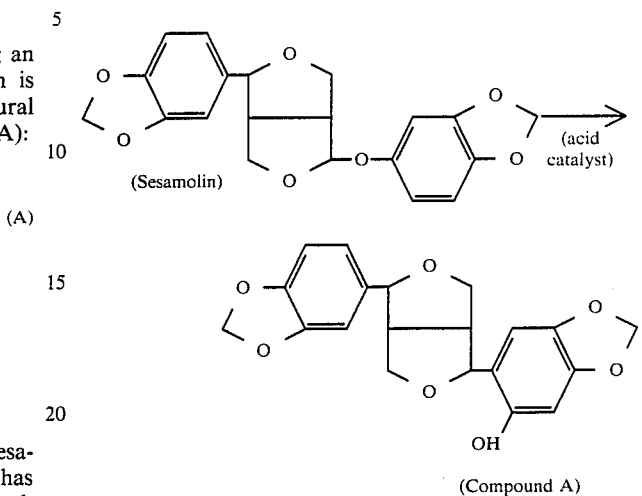

Sesamolin, which is used in the present invention, is contained by about 0.15–0.3% in sesame seeds and by about 0.3–0.6% in raw sesame seed oil obtained by mechanically compressig raw or roasted sesame seeds or by using organic solvent such as hexane for extraction from sesame seeds. Sesame seeds and such raw sesame seed oil may therefore be used as the source of sesamolin but, since a relatively high concentration of sesamolin is also known to be present in the distillate (or so-called deodorized scum) obtained by distillation of raw sesame seed oil with steam under normal or reduced pressure to deodorize it, such deodorized scum can be advantageously utilized as the source material for sesamolin.

According to the present invention, sesamolin is condensed or isolated from such a source material by extraction with a solvent or by a method such as precipitation with cooling, distillation and filtering in a solvent system. More in particular, sesamolin with high purity can be obtained by a recrystallization method in a solvent system or by partial extraction type column chromatography (for example, *J. of American Oil Chemical Soc.*, 31, 302 (1954)). Thereafter, acid catalyst is applied to condensed or isolated sesamolin. The acid catalyst for this purpose may be a Brφnsted acid, a Lewis acid or a solid catalyst having the functions of an acid catalyst. Use may be made, for example, of various inorganic and organic Brφnsted acids such as sulfuric acid, phosphoric acid, boric acid, p-toluene sulphonic acid and camphorsulphonic acid, Lewis acids such as aluminum chloride, titanium chloride, tin chloride and boron trifluoride, and solid catalysts with the functions of acid catalyst such as acid clay, activated clay, zeolite, silica-titanium oxide and cation exchange resins. They may be used singly or two or more of them may be used together as a combination.

There is no particular limitation regarding the amount of acid catalyst to be used, but it is preferably 0.05–10 wt % with respect to sesamolin in the case of a Brφnsted acid or a Lewis acid and 1–50 wt % in the case of a solid catalyst. It should be avoided to use an excessive amount of solid catalyst because, although the reaction itself is not affected adversely, Compound A produced in the reaction becomes adsorbed by the catalyst layer and its yield drops.

An acid catalyst may be directly applied to condensed or isolated sesamolin at a temperature above its melting point. From the point of view of simplicity of operation, however, it is preferable to dissolve condensed or isolated sesamolin in an inactive solvent such as an aromatic hydrocarbon like benzene, toluene and xylene or a halogenated hydrocarbon having no active hydrogen group and to then apply an acid catalyst. The acid catalyst is usually applied at a temperature above 50° C., or preferably in the range of 70°–200° C. If use is made of an inactive solvent as disclosed above, therefore, the temperature range is from 50° C. up to the boiling point of such an inactive solvent. In any case, the acid catalyst need not be dissolved in the reacting system and may be a non-uniform system. When the reaction is in an industrial scale, however, it is preferable to make use of a solid catalyst with the functions of an acid catalyst because operations such as removal of the catalyst after the reaction can be performed more conveniently.

In order to produce Compound A profitably according to the present invention, it is necessary that the acid catalyst be applied under a condition where no compounds having an active hydrogen group such as water, alcohols and phenols participate in the reaction. This is because side reactions such as hydrolysis and alcoholysis of sesamolin by such an active hydrogen compound would become dominant in the presence of an acid catalyst. If water is present for example, sesamol and sesamin are produced in the presence of an acid catalyst by hydrolysis of sesamolin. One method of preparing a reaction system wherein active hydrogen compounds do not participate in the reaction is to remove the water and alcohol contents of the condensed or isolated sesamolin and the acid catalyst by drying or removing the solvent before they are used for the reaction. Another method is to add them to an inactive solvent as explained above and to remove water and alcohols by heating and refluxing for azeotropy.

After such a reaction, Compound A or a substance containing Compound A is obtained through processes involving neutralization, filtering, extraction, removal of solvent, etc. The product may be used directly as an active antioxydant or may be subjected to a separation process or the like to further improve the concentration of Compound A. Other active antioxydants or synergists may be appropriately mixed together.

In what follows, the present invention is explained further by way of examples:

EXAMPLE NO. 1

Placed in a reactor equipped with a stirrer, a thermometer and a condenser with a Dean-Stark separator were 20 g of sesamolin and 200 ml of toluene. After sesamolin was dissolved, the mixture was heated to remove the water content by azeotropy. After the mixture was cooled to 80° C., 0.1 g of camphorsulphonic acid was added for a reaction at 80° C. for 60 minutes. The reaction liquid was analyzed by HPLC to study the peak appearing at 11.8 minutes. Compound A was obtained with a yield of 82.4%. The HPLC analysis was carried out with a column of 8 mm$\phi \times$250 mm filled with Deverocil ODS-10 ™ (by Nomura Chemical Co., Ltd.). The solvent was methanol/water=6/4 and its flow rate was 5.0 ml/min.

EXAMPLE NO. 2

Placed in a reactor as described in Example No. 1 were 200 ml of toluene and 2 g of cation exchange resin of sulphonic acid type and the mixture was heated to remove its water content by azeotropy. After it was cooled to 80° C., 20 g of sesamolin was added. After a reaction at 80° C. for 30 minutes, the cation exchange resin of sulphonic acid type was removed by filtering and the solvent was removed by means of an evaporator to obtain 19 g of light brown solid. It was subjected to a HPLC analysis as described in Example No. 1 and Compound A was obtained with a yield of 73.6%.

EXAMPLE NO. 3

Placed in a reactor were 20 g of sesamolin and 1 g of acid clay and the mixture was heated to 140° C. in dry nitrogen vapor. After 30 minutes of reaction with shaking, 18 g of light brown solid was obtained by filtering. It was subjected to a similar HPLC analysis and found to contain 12.8 g of Compound A.

EXAMPLE NO. 4

Raw sesame seed oil was obtained from Chinese sesame seeds by using an expeller. After a water soluble solution of sodium hydroxide was used to remove free fatty acid therefrom, it was washed with water and then dehydrated. It was further decolored with active charcoal and deodorized at 210° C. and 4 mm Hg. Dissolved in 500 ml of xylene was 100 g of deodorized scum thus collected. To this were further added 300 ml of isopropyl alcohol and 200 ml of 1N water solution of sodium hydroxide. After the mixture was carefully stirred, it was left quietly for separation. The isopropyl/water layer was removed and was then washed with water until the xylene layer became neutral to remove free fatty acid. A brown semi-solid substance was obtained when a portion of this xylene layer was dried. It was then subjected to a HPLC analysis and found to contain 51% of sesamin and 17% of sesamolin. The aforementioned xylene layer was heated to remove isopropyl alcohol and after water was further removed by azeotropy, 1 g of acid clay was added and the mixture was stirred for 30 minutes in reflux. After it was left to cool, the acid clay was removed by filtering and 67 g of a brown semi-solid substance was obtained by removing the solvent. This was subjected to a HPLC analysis as done in Example No. 1 and found to contain 8.2g of Compound A but no sesamolin was detected.

EXAMPLE NO. 5

Dissolved in 500 ml of benzene was 100 g of deodorized scum obtained by the same process as in Example No. 4. To this were further added 300 ml of isopropyl alcohol and 200 ml of 1N water solution of sodium hydroxide. After the mixture was carefully stirred, it was left quietly for separation. The isopropyl alcohol/water layer was removed, and it was then washed with water until the benzene layer became neutral to remove free fatty acid. Solvent was removed from this benzene layer by an evaporator and 69 g of brown solid substance was obtained by drying. After this was dissolved in 200 ml of benzene, 0.5 g of aluminum chloride was added to it for a reaction of 30 minutes in reflux. After it was cooled to room temperature, 200 ml of isopropyl alcohol and 100 ml of 1N water solution of sodium hydroxide were added. The mixture was thoroughly shaken and then left quietly for separating an isopropyl alcohol/water layer. The pH of this layer was adjusted to 2 with hydrochloric acid and 200 ml of benzene was added. After the mixture was thoroughly shaken, it was left quietly and the separated benzene layer was washed until the washing water became neutral, dehydrated with anhydrous sodium sulfate and filtered. Solvent was then removed and 8.6 g of light brown solid substance was obtained. It was subjected to a HPLC analysis as in Example No. 1 and found to contain Compound A by 84%.

COMPARISON EXPERIMENT NO. 1

Placed in the same reactor as used in Example No. 1 was 20 g of sesamolin with 200 ml of toluene. After it was dissolved, it was heated to remove water by azeotropy. After it was cooled to 80° C., 0.1 g of camphorsulfonic acid and 5 g of water were added for a reaction at 80° C. for 60 minutes. The reaction liquid was subjected to a HPLC analysis as in Example No. 1 and found to contain sesamol by 74% but only a trace of Compound A. A HPLC analysis of sesamol was similarly performed as explained in connection with Example No. 1 except the solvent was methanol/water=3/7, its flow rate was 4.0 ml/min and retention time was 10.4 min.

COMPARISON EXPERIMENT NO. 2

It was carried out identically to Comparison Experiment No. 1 except use was made of 5 g of ethanol instead of 5 g of water and Compound A was obtained with yield of 13.6%.

TESTS ON ANTIOXYDATION ACTIVITY

Taken individually into Erlenmeyer flasks with the capacity 100 ml were 3.7 mg (0.01 m mole) of Compound A isolated by HPLC from the product obtained in Example No. 3, 3.7 mg of the product in Example No. 5 and, for comparison, 0.01 millimole each of sesamolin, sesamol and dl-α-tocopherol, and 20 g of soya-bean oil refined by passing through a basic alumina column was added to each flask. After the flasks were thoroughly shaken, they were kept in an oven at 98° C. and their peroxide values were measured over periods of time by a known method. The results of measurements are shown in Table 1.

TABLE 1

| | Peroxide Value (meq/kg) | | | | | |
|---|---|---|---|---|---|---|
| | 0 | 3 | 5 | 7 | 10 | 15 hours |
| Compound A | 3.2 | 9.4 | 16 | 26 | 42 | 67 |
| Product in Example 5 | 3.2 | 11 | 17 | 26 | 44 | 78 |
| Sesamolin | 3.2 | 54 | 95 | 137 | 200< | — |
| Sesamol | 3.2 | 11 | 35 | 62 | 140 | 200< |
| dl-α-tocopherol | 3.2 | 13 | 18 | 24 | 40 | 99 |
| none | 3.2 | 59 | 98 | 140 | 200< | — |

Table 1 clearly shows that superior active antioxydants with Compound A as principal ingredient can be produced by an entirely novel, industrially feasible process of applying an acid catalyst to sesamolin.

What is claimed is:

1. A method of producing an active antioxydant comprising the step of obtaining a compound having the structural formula (A) shown below

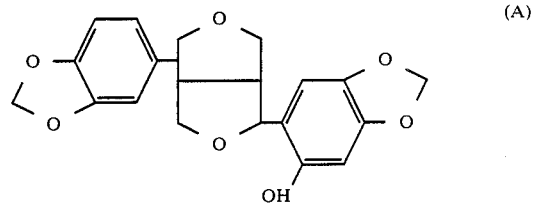

by applying an acid catalyst to sesamolin in an environment characterized as substantially preventing hydrolysis or alcoholysis of sesamolin from becoming dominant.

2. The method of claim 1 wherein said acid catalyst is applied to sesamolin in an inactive solvent without active hydrogen groups.

3. The method of claim 1 wherein said acid catalyst includes one or more kinds of solid catalysts with acid catalyst characteristics selected from a group consisting of acid clay, activated clay, zeolite, silica-titanium oxide and cation exchange resins.

4. The method of claim 2 wherein said acid catalyst includes one or more kinds of solid catalysts with acid catalyst characteristics selected from a group consisting of acid clay, activated clay, zeolite, silica-titanium oxide and cation exchange resins.

5. The method of claim 1 wherein said acid catalyst includes at least one kind of Brϕnsted acid.

6. The method of claim 2 wherein said acid catalyst includes at least one kind of Brϕnsted acid.

7. The method of claim 5 wherein said Brϕnsted acid is organic.

8. The method of claim 5 wherein said Brϕnsted acid is inorganic.

9. The method of claim 5 wherein said acid catalyst includes both organic and inorganic Brϕnsted acids.

10. The method of claim 6 wherein said Brϕnsted acid is organic.

11. The method of claim 6 wherein said Brϕnsted acid is inorganic.

12. The method of claim 6 wherein said acid catalyst includes both organic and inorganic Brϕnsted acids.

13. The method of claim 1 wherein said environment is further characterized substantially by the absence of active hydrogen compounds which cause hydrolysis or alcoholysis of sesamolin

* * * * *